(12) United States Patent
Landesberg

(10) Patent No.: US 6,511,413 B2
(45) Date of Patent: Jan. 28, 2003

(54) SINGLE CANNULA VENTRICULAR-ASSIST METHOD AND APPARATUS

(75) Inventor: Amir Landesberg, Haifa (IL)

(73) Assignee: Levram Medical Devices, Ltd., Nesher (IL)

( * ) Notice: Subject to any disclaimer, the term of this patent is extended or adjusted under 35 U.S.C. 154(b) by 0 days.

(21) Appl. No.: 09/858,343

(22) Filed: May 16, 2001

(65) Prior Publication Data

US 2002/0173693 A1 Nov. 21, 2002

(51) Int. Cl.[7] ............................................. A61N 1/362
(52) U.S. Cl. ........................... 600/17; 600/16; 623/3.28
(58) Field of Search ...................... 600/16–18; 623/3.28

(56) References Cited

U.S. PATENT DOCUMENTS 6,293,901 B1 * 9/2001 Prem ........................... 600/16

* cited by examiner

Primary Examiner—George R. Evanisko
Assistant Examiner—Omar Khan
(74) Attorney, Agent, or Firm—Herbert Dubno

(57) ABSTRACT

A system for assisting the failing ventricle, which utilizes a single blood displacement chamber and a single cannula. The cannula is inserted into the failing ventricle cavity and is connected to a blood displacement actuator. The device produces blood displacement at a critical time for a critical duration and with blood flow time course such that it improves the systolic function of the heart: augments the cardiac output and increases the generated pressure. The device also improves the diastolic function by increasing the ventricle compliance and imposing rapid relaxation of the ventricle wall. The device provides additional external work without deteriorating the mechanical function of the failing ventricular, moreover it decreases the energy consumption of the failing heart and improves the coronary perfusion. Consequently, the device improves the balance between the energy supply (coronary perfusion) to the ventricle wall and the mechanical demands, and allows recovery of the failing heart.

9 Claims, 11 Drawing Sheets

SINGLE CANNULA VENTRICULAR-ASSIST METHOD AND APPARATUS

FIELD OF THE INVENTION

The present invention relates to a ventricular-assist method and apparatus and, more particularly, to a ventricular-assist device (VAD, which utilizes only a single cannula and can assist both the acute and chronic failing heart. The device can be used as bridge to recovery of the failing heart, as a permanent implanted assist device or as a bridge to transplantation or as a bridge to other Cardiac Assist Devices. The invention also relates to a method of sustaining the failing heart utilizing a ventricular-assist device and an algorithm for operating a ventricular-assist device.

BACKGROUND OF THE INVENTION

The normal range of cardiac output, normalized to total body surface, is wide, 2.5 to 3.8 liter per minute per one square meter ($1/min/m^2$). In general, cardiac assist is necessary whenever a patient's cardiac output drops below the adequate blood supply needed to sustain proper blood perfusion, which is around 2 $1/min/m^2$. Failure of the cardiac ventricle to contract and to eject the blood out of the ventricle and thereby to supply adequate flow is defined as "systolic failure". However, more than 50% of the patients over 60 display inadequate ventricle filling and tissue congestion, which is defined as "diastolic failure". Cardiac assist is used to treat patients suffering from heart failure at a stage where conventional drug therapy proves ineffective.

Cardiovascular diseases (CVD) represent the leading cause of death in the industrialized world. CVD claimed 960,592 lives in the US in 1995 (41.5% of all deaths for that year).

Congestive Heart Failure (CHF) is a chronic disorder that develops over time, manifested clinically by an enlarged heart and symptoms and signs of low cardiac output and tissue congestion. The low cardiac output leads to decreased blood perfusion to vital organs (liver, kidney and brain). The CHF is also characterized by lung congestion (recurrent pulmonary edema), which threatens life and requires frequent hospitalization. CHF is associated with profound symptoms that limit daily activities, is a debilitating disease with poor quality of life. CHF is the most common cause of hospitalization of patients over 60 years of age.

According to the US National Heart Lung and Blood Institute (NHLBI) and the American Heart Association there are approximately 5 million patients who suffer from Congestive Heart Failure (CHF) in the US and between 400,000 and 500,000 newly diagnosed patients each year. Long-term survival rates are low and the 5 year mortality rate for patients with CHF is 75% in men and 62% in women, while in patients with decompensated heart failure the mortality rate is 60% per year.

CHF has various etiologies, including cardiovascular disease (diseases which affect blood flow to the myocardium), chronic hypertension (high blood pressure), incompetent valves, inflammation of the heart muscle or the valves, substance (amyloid) accumulation and congenital heart problems.

Patients suffering from Congestive Heart Failure (CHF) are initially treated with medication. While conventional drug therapy may delay the progress of CHF, it is not curative. Cardiologic intervention (such as Angioplasty and Stenting), surgery (Heart by-pass surgery, Cardiomyoplasty, Partial Ventriculectomy known as Batista's procedure), and mechanical devices are often considered when drug therapies prove ineffective or inadequate. Electrical disturbances of the heart that threaten or impair the quality of the patient's life have been treated effectively with pacemakers and implantable defibrillators. However, congestive heart failure has not been addressed effectively. Currently, the only available method of treating end-stage CHF is a heart transplant.

The demand for temporary and permanent cardiac-assist devices for the treatment of chronic heart failure is remarkably large; in 1993 between 40,000 to 70,000 patients needed life-sustaining assist devices or a total artificial heart, and an additional 80,000 to 200,00 patients needed quality of life improvements by surgery (Cardiomyoplasty or Heart Booster).

Ventricular-assist devices are needed for:

1. Bridge-to Transplantation—patients awaiting heart transplants and who are not scheduled and when the heart failure is unresponsive to medical treatment.

2. Bridge-to-Recovery—cardiac assist for patients whose heart has sustained serious injury, but can recover if adequately supported. This includes the use of a cardiac-assist device after open heart surgery in order to provide support until the heart regains its ability to pump, and severe myocardial infarction refractory to conventional treatment with medication. Temporary cardiac support is intended primarily to:

a) Prevent or reduce damage to vital organs (brain, kidneys) from cardiac failure and to support adequate blood circulation.
   b) Allow the failing heart to recover, i.e. to provide adequate coronary perfusion to the heart itself.
   c) Reduce the energy consumption of the failing heart and to improve the balance between energy supply and demands.

3. Permanent support for the failing heart, for patients that are not candidates for heart transplantation.

Existing temporary mechanical cardiac devices are divided into three groups:

1. Temporary cardiac assist for several hours, as the intra-aortic balloon that is frequently utilized for patients with heart failure after open-heart surgery, due to failure to wean from the cardiopulmonary bypass.

2. Long-term (days, weeks, months) Ventricular Assist Device (VAD), as a bridge to heart transplantation or a bridge to recovery.

3. Permanent support by permanent VAD or by Total Artificial Heart (TAH).

Intra Aortic Balloon Pump (IABP). The IABP has been in clinical use for over 30 years. The IABP consists of a balloon (30–50 ml) that is inserted into the descending aorta and is inflated during the diastole and deflated during the systole. The IABP increases the cardiac output by less than 0.5 $1/min/m^2$. Consequently, although it was designed to assist a failing heart by improving blood perfusion, it requires a certain threshold level of cardiac output and cannot take over the pumping function of the heart. As a result, it can only be utilized in treatment of patients who require mild levels of mechanical assistance (unless there is a supplemental assisting heart device).

The main advantages of the IABP are that it increases the coronary flow and decreases the afterload (the work against which the ventricle works). Hence the device improves the energy supply to the myocard, reduces the energy consumption and allows the heart to recover. However, the IABP is used only for short-term circulatory assist due to high risk of severe thromboembolic complications.

Ventricular Assist Devices (VAD)—VADs take over the complete pumping function of one or both sides of a failing heart. They unload the assisted ventricle. Left Ventricular Assist Devices have been approved for use by the FDA as bridge-to-heart transplantation, to keep alive those awaiting a donor heart. These devices have also been approved by the FDA for use by patients whose hearts are in failure but may be able to recover by reducing the myocardial work (unloading), including patients in postsurgical life-threatening heart failure.

More than a dozen companies are developing devices, ranging from left-ventricular assist products to total artificial hearts, that offer CHF patients either longer-term support with an alleviation of symptoms, and/or an alternative to heart transplant. Some of these (Thermo CardioSystems, Thortec, Abiomed and Baxter Healthcare) have ventricular assist products on the U.S. market. Ventricular-assist devices are generally employed on a temporary basis, with treatment periods ranging from a few hours to a few weeks, or at most, a limited number of months. However, some devices have been designed for long-term use and can be considered lifetime support systems. However, to date, such lifetime support is still in developmental and experimental stages and has not been approved by the FDA.

The currently available assist devices can be sorted by the following major three criteria:
1. Mode of operation:
   a. Bypass circulation.
   b. Direct mechanical actuator.
2. Type of flow: Pulsatile or non-pulsatile flow.
3. Location: implanted devices or extra-corporeal devices.

Most of the available VADs in the market belong to the bypass group. There are four major types of these VADs: Roller pumps, Centrifugal pumps, Pneumatic devices and Electrical devices. These devices differ in design, indications and duration.

Roller and Centrifugal Pumps are approved for short-term (i.e. hours) support of patients undergoing heart surgery. These devices generate a non-pulsatile blood flow which severely restricts the time patients can safely remain on support. They also require additional medical personnel to provide constant monitoring and ensure that the pump is operating correctly. Recently, new centrifuge pumps are being developed that are highly a efficient (low energy consumption) and can be implanted for prolonged assist.

The pneumatic devices can provide full circulatory assistance and were the first to be approved for clinical use. The BVS 5000, developed and manufactured by Abiomed Inc. was also approved by the US FDA as a bridge-to-recovery device for the treatment of reversible heart failure. The BVS-5000 (BVS) is a pneumatic extra-corporeal, bi-ventricular assist device, allowing the heart to rest and recover its function. However, the blood circulates out of the body and the patient cannot be ambulatory. The company's first full year of marketing the BVS in the US was 1994.

Thoratec Laboratories Corporation has developed an implantable pneumatic-assist device, which is connected to an external-drive by a percutaneous air-drive line. This system was also approved by the FDA as a bridge to heart transplant.

The electrical VAD are completely implantable with an implantable controller, battery and charger (secondary coil). The main electrical pulsatile implantable pumps are: Novacor N-100 (Baxter Healthcare Corp.), Heartmate 1000 NE LVAS (ThermoCardioSystem Inc.) and Pennsylvania State University System.

In September 1998, the first two ambulatory implantable left ventricular-assist systems (LVAS), from Baxter and ThermoCardioSystem Inc (TCS), were approved in the U.S. TCS' implantable electric HeartMate LVAS has been marketed since 1994. In Europe, the Baxter Novacor LVAS has been approved as a commercial product since 1994. These devices represent a significant advance over first-generation technology, since they allow patients to live outside the hospital while awaiting transplantation. The Baxter Novacor is an electromechanical pump that is implanted in a patient's abdomen and connected to the left ventricle of the heart. The system is operated by an external, portable electronic controller, and is powered by battery packs, which the patient typically wears around the waist in a shoulder vest or backpack. Nearly 900 patients worldwide have received the Novacor LVAS: two patients have currently been supported for more than three years by their original devices. In Europe, the device has helped to rehabilitate some patients' hearts to the extent that neither VAD assistance, nor heart transplant were necessary.

Transplant bridging, and possibly long-term cardiac assistance may also be accomplished with implantable axial flow and centrifugal pumps. An axial flow VAD, that includes a high-speed rotor, has been recently developed by Micromed in co-development with the National Aeronautics and Space Administration (NASA). This miniaturized DeBakey/Ventricular Assist Device (30 mm×76 mm) weighs only 93 grams, making it about one-tenth the size of portable heart-assist devices already on the market.

Examples of companies pursuing cardiac-pumping technology include: Jarvik Research, Medtronic Inc., 3M Corporation Inc., Kirton Medical, Micromed Technology and Cardiac Assist Technologies.

Direct Mechanical Actuator

Unlike all the above VAD's that pump the blood out of the ventricle into the aorta and bypass the failing heart, the Direct Mechanical Actuator proposes a different approach, taken by Cardio Technologies. This company is pursuing a cuff-like device that is placed around the outside of the heart. This device applies external pressure to enhance blood flow. A somewhat similar device, designed to reduce the size of an enlarged heart, is under development by Acorn Cardiovascular. Abiomed was also involved in some early development stages of the Heart Booster system designed to wrap around the heart, to provide ventricular augmentation.

Alternative Surgical modalities

Three additional surgical methods have been developed recently as alternatives to cardiac assist, in order to improve the residual cardiac function: 1) Dynamic Cardiomyoplasty; 2) Partial Ventriculectomy or Batista operation, and 3) Percutaneous transmyocardial revascularization (PTMR). However, these methods are controversial.

In the Dynamic Cardiomyoplasty technique, a surgeon wraps some of the patient's skeletal muscle around the weakened heart and stimulates the repositioned muscle to synchronously squeeze the heart during systole. Dynamic Cardiomyoplasty is highly invasive and involves complicated surgical procedures. Medtronic is also involved in clinical studies of this pacemaker-aided technique using the latissimus dorsi muscle. Percutaneous transmyocardial revascularization (PTMR) is a recently approved catheter-based laser technique that involves drilling about 50 tiny holes in the left ventricle to improve blood flow to the heart muscle. This laser surgery was suggested as a cost-effective alternative to transplantation for certain patients with severe angina, who were not candidates for angioplasty or bypass surgery. The precise mechanism underlying this approach is controversial. Moreover, the efficacy of this method is under investigation.

OBJECTS OF THE INVENTION

It is the principal object of the present invention to provide an improved ventricular-assist device that, has the following advantages over the current available VADs:

a. Simple Implantation. It allows cannulation and implantation by minimal invasive approach. This will shorten the surgery and the postoperative recovery and hospitalization for rehabilitation.

b. Allows bridge to recovery of the failing heart, i.e. it should improve the viability and function of the residual cardiac tissue of a failing heart. The mode of operation is based on the physiological characteristics of the cardiac muscle, so that it will allow the failing heart to recover by the augmentation of the coronary perfusion and by decreasing the energy consumption and supporting the cyclic heart function (decreasing the end diastolic volume while increasing the systolic pressure and the stoke volume). The device should be free from the drawbacks of bypass (shunting) devices which unload the failing heart and may lead to atrophy, endocardial ischemia and right heart failure.

c. Economical energetically, so that it allows prolonged support on rechargeable portable or implanted power supply.

d. No valves are required—which allow prolonged durability.

e. Utilizes only a single short conduit, thereby decreasing the likelihood of thrombo-embolic complications.

f. Imposes few physiological shear stresses on the blood, and hence avoids the complication of hemolysis, encountered in the axial flow devices.

It is also an object of the invention to provide an improved method of assisting a failing heart while attaining some or all of the aforementioned advantages.

Still a further object of the invention is to provide a method of and an apparatus for ventricular assistance whereby drawbacks of earlier systems can be avoided. The assistance provided can be more reliable and the energy drain on the assisted heart can be minimized.

SUMMARY OF THE INVENTION

These objects are attained, in accordance with the invention in a ventricular-assist method, which comprises:

(a) inserting into the failing ventricular cavity (left, right or both) of a failing heart through a wall thereof a respective cannula connected to a blood displacement chamber and actuator;

(b) in cadence with normal functioning of the failing heart, effecting flow of blood into the failing ventricular cavity (inflow), generated by the blood displacement actuator, with each heart beat. The inflow from the displacement chamber commences only after opening of an outlet valve of the respective ventricular cavity of the failing heart or only after a detected shortening of a monitored region of a wall of the respective failing ventricle, and continues during an ejection phase of the respective ventricle, thereby augmenting ejection volume (stroke volume) from the respective ventricular cavity by up to a maximum volume of blood inflow, into the respective ventricle, per systolic phase;

(c) controlling a time course of blood flow through the cannula, generated by the blood displacement actuator, into the ventricular chamber (inflow) in step (b) to reduce the shortening of a respective ventricular wall of the failing heart by comparison with ventricular wall shortening while the device does not provide assist (inflow), and to prevent ventricular wall stretching (eccentric work). (Controlling the inflow time course allows augmentation of the systolic pressure within the respective failing ventricle);

(d) controlling an increase in the total ejected volume out of the ventricular outlet with the blood displacement actuator. (The ventricular outflow is the sum of contribution of the ventricular wall shortening and the VAD inflow into the ventricle);

(e) retracting blood from the ventricular chamber through the same cannula (outflow), immediately upon closing of a respective outlet valve of the failing ventricle.

The method of the invention further comprises the steps of:

monitoring ventricular wall motion and the intraventricular pressure during blood flow into the ventricular chamber (inflow), generated by the blood displacement actuator, through the cannula in steps (b, c); and controlling a profile of blood flow into the ventricle thereof to decrease the measured ventricular wall motion thereby obtaining an increase in the pressure within the respective cavity and increasing the cardiac output.

According to the invention, at least one parameter of ventricular wall shortening and at least one parameter of ventricle output can be measured during the cardiac cycle and in response to measurement of these parameters, selectively either in real time or by beat-by-beat computation, blood flow into the ventricle chamber and out of the ventricle chamber are controlled by the blood displacement actuator, to correspond to the desired cardiac output (ejected volume)and profile of blood flow.

The parameters of wall shortening which can be monitored are the ventricular volume, ventricular diameters, and ventricular wall strains or the ventricular out-flow in preferred embodiments of the invention.

The cannula is connected on the opposite side of the cardiac wall insertion to the blood displacement chamber, which is connected to the actuator with a computer-controlled pushing (inflow) and retracting (outflow) blood mechanism, into and out of ventricular cavity through the cannula inserted into the failing ventricular cavity (right, left, or both).

In another aspect of the method, the following steps are carried out:

(a) inserting into a failing ventricular cavity (left, right or both) of a failing heart through the cardiac wall thereof a respective cannula;

(b) in a cadence with normal functioning of the failing heart, generating inward blood flow (inflow) with the blood displacement actuator, through the respective inserted cannula with each heart beat. The inward blood flow commences only after opening of an outlet valve of the respective ventricular cavity of the failing heart or only after a detected shortening of a monitored region of a wall of the respective ventricular cavity of the failing heart and continues during an ejection phase of the respective ventricular cavity, thereby augmenting ejection volume from the respective ventricular cavity by up to a maximum of the blood flow volume through the respective inserted cannula into ventricular chamber per systolic phase;

(c) controlling a time course of blood flow through the respective inserted cannula into ventricle chamber in step (b) to reduce a shortening of a respective ventricular wall of the failing heart by comparison with ventricular wall shortening while the device does not assist the circulation (does not provide the inflow), and to prevent ventricle wall stretching (eccentric work);

(d) controlling an increase in the total ejected volume out of the ventricular outlet as defined by the sum of contribution of the ventricular wall shortening and the VAD inflow into the ventricle;

(e) retracting blood through the cannula from the ventricle (outflow) immediately upon closing of a respective outlet valve of the failing heart.

The apparatus can have a computer receiving input from the sensor and controlling the blood displacement actuator with an output. The computer is programmed for each heartbeat (n) to:

(a) evaluate cardiac output and work at the $n^{th}$ beat;

(b) compare the evaluated cardiac output and work at the $n^{th}$ beat with a desired cardiac output to determine an amplification factor ($A_F$);

(c) multiply the amplification factor ($A_F$) by a weighting function (W(t)) as determined by an operator to generate a magnitude of a feedback loop;

(d) evaluate ventricle wall shortening ($S_n(t)$) and compare the evaluated wall shortening with a desired wall shortening (Des(t)) to obtain a difference $Err_n(t)=Des(t)-S_n(t)$;

(e) generate the inflow function $EXP_{n+1}(t)=EXPN_n(t)+A_F*W(t)*Err_n(t)$; and (f) control the profile of the blood inflow into ventricle at a next beat (n+1).

The amplification factor ($A_F$) is multiplied by a weighting factor (w(t)) at each beat where $0 \leq W(t) \leq 1$ and $0 \leq t \leq T$, where t=0 is the time onset of the inflow and t=T is the end of ejection (systole).

Advantageously the computer is a computer, which controls the inward flow profile at the next beat (n+1) by regulating the onset time of the inflow and the profile function of inflow. The computer a) calculates the desired profile of the inflow and outflow through the cannula, either in real time or by repetitive iterations and corrections, from beat to beat; and b) regulates in real time, the timing of the inflow and outflow based on the monitored above sensors.

The computer can receive input from the sensor and can control the blood displacement actuator with an output. The computer being programmed for each heartbeat (n) to:

(a) evaluate cardiac output and work at the $n^{th}$ beat;

(b) compare the evaluated cardiac output and work at the n beat with a desired cardiac output and determine an amplification factor that will not cause ventricle wall stretch in part based upon additional inputs;

(c) evaluate ventricle wall shortening ($S_n(t)$) at the $n^{th}$ beat and providing the ventricle wall shortening as one of the additional inputs;

(d) detect possible ventricle wall lengthening from the evaluation of the wall shortening in step (c) and providing therewith another of the additional inputs, and triggering an alarm upon ventricular wall lengthening;

(f) determine a time course of blood flow from blood displacement actuator through the cannula into the ventricular chamber from the amplification factor and a desired profile of blood inflow; and (g) generate a blood inflow function representing the time course of the control of the blood displacement actuator at a next beat (n+1) with the inflow function.

The means for detecting a state of the outlet valve can include at least one of the following:

a pressure sensor for measuring intraventricular pressure.

a pressure sensor for measuring aortic pressure or a gradient between intraventricular and aortic pressure;

ultrasound or electrical impedance means for measuring intraventricular volume or ventricle diameters;

a Doppler or an ultrasonic or electromagnetic flow meter measuring ventricle outlet flow;

strain gauges for measuring ventricle wall shortening;

a heart sound monitor; or a cardiac electrical activity measuring device.

BRIEF DESCRIPTION OF THE DRAWING

The above and other objects, features, and advantages will become more readily apparent from the following description, reference being made to the accompanying drawing in which.

SPECIFIC DESCRIPTION

Figure 1:
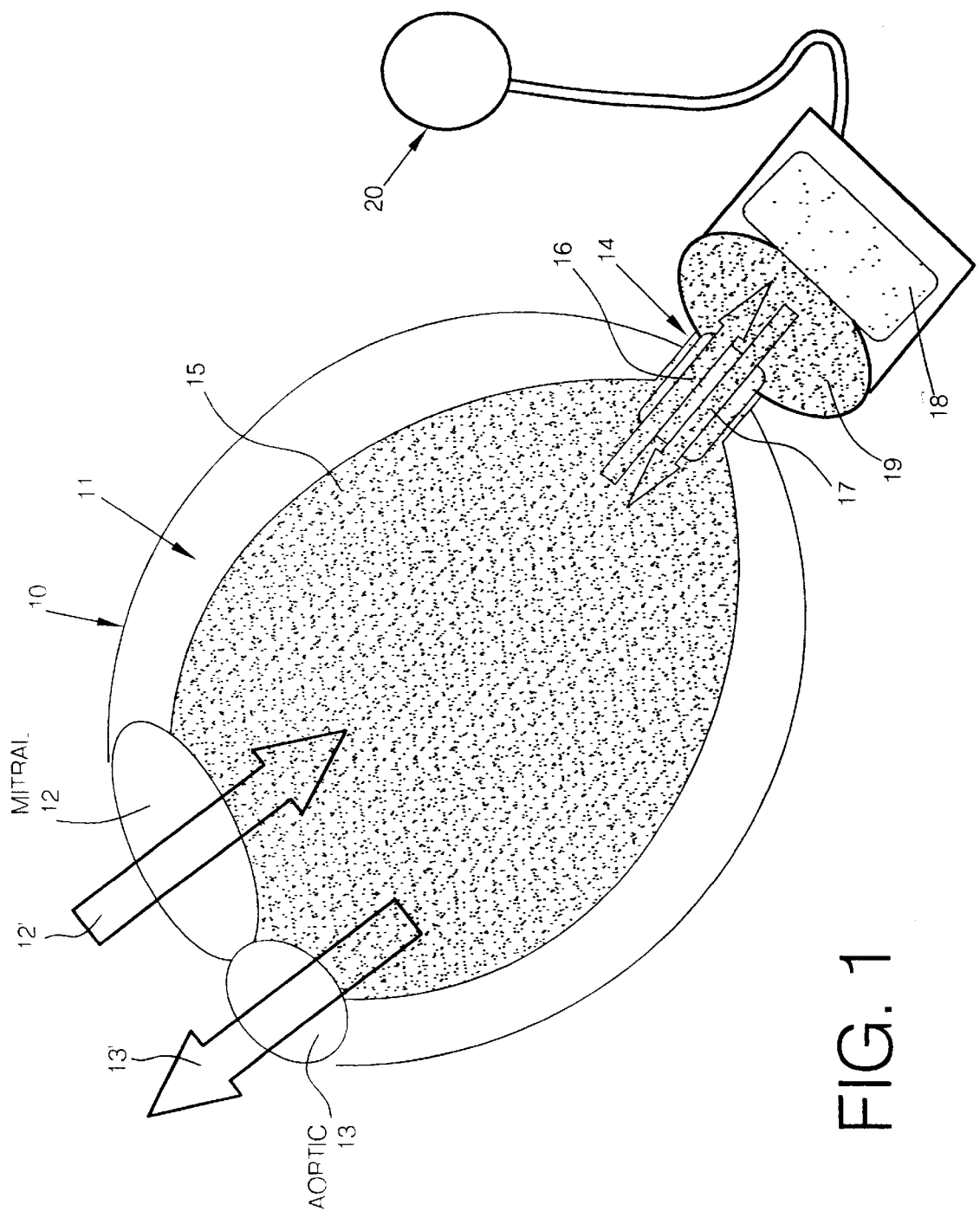
FIG. 1 is a diagram illustrating the use of the ventricular-assist device to assist the failing ventricle, showing a cannula inserted into the failing ventricle and connected to the displacement chamber, to allow the back and forth blood flow (indicated by the solid arrows).

FIG. 1 shows the application of the device of the invention to a failing left ventricle. Reference may be related to my commonly owned copending application Ser. No. 09/517,834 filed Mar. 2, 2000 whose principles are applicable to the present invention and which is therefore incorporated wholly herein by reference. The ventricular-assist can also apply to the failing right ventricle or to both ventricles in which each can be provided with an independent assist device according to this invention.

The left ventricle 10 of a failing heart has been shown and comprises the ventricle wall 11, the inlet from the auricle or the mitral valve 12 and the outlet to the arterial system or aortic valve 13. A cannula 14 is inserted into the ventricle cavity 15 and allows inflow and outflow of blood as described by the solid arrows 16 and 17 from a blood displacement chamber 19. The blood displacement chamber 19 is actuated by the actuator 18. The blood is pushed inward (inflow into the ventricle) and outward (outflow from the ventricle) and into the displacement chamber 19 as controlled by the actuator 18. Thus the VAD of the invention consists of only one chamber 19 and one cannula 14. An implanted device, which is placed inside the thorax or the upper abdomen is equipped with a compliance chamber 20 filled with air, to allow the small displacement of the displacement chamber 19. However, for an extra-corporeal device, where the actuator and the displacement chamber are placed close to the chest (bedside console) there is no need for a compliance chamber 20. The actuator can be any pneumatic, hydraulic, electrical or electromechanical device capable of providing a force sufficient to displace the blood through the cannula.

The device of the invention is not intended to replace the entire function of the failing heart but merely to add additional cardiac output, thereby increasing a low level natural cardiac output of around 2 liters per minute by up to, say, two additional liters per minute. Assuming a heart rate of about 70 per minute, the added stroke volume is of less than 30 ml/beat and hence the volume of the displacement chamber can be less than 30 ml.

The VAD of the invention improves the systolic function of the ventricle by increasing the ability of the heart to eject blood out of the ventricle outlet (outline arrow 13') due to the external work added by the actuator. The increase in the ejected volume results from an increase in the ventricular cavity pressure and the combined contribution of the inflow from the actuator and the failing heart shortening.

The improved systolic function and the increase in the systolic pressure is obtained by changing the loading condition imposed on the ventricle wall. The decrease in the failing heart shortening allows the failing heart to increase the generated pressure.

The VAD improves also the failing ventricle filling (outline arrow 12') during the diastole (diastolic function) by imposing rapid cardiac wall shortening during early relaxation, which causes rapid deactivation of the ventricle wall and increases the ventricle compliance.

During systole the device produces less than 1.6 watts of external work and the average (systole and diastole) power is less than 0.5 watts. Consequently, from heat and energy considerations, with reasonable electromechanical efficiency a device based on the suggested mode of operation can be implanted inside the thorax, and energized by an implanted battery or other prime mover.

To summarize, the main concepts are:
(a) Insertion of the cannula into the ventricle cavity.
(b) Control of the appropriate timing of the device inflow and outflow, under real time control.
(c) Control of the appropriate volume and profile of the blood inflow and outflow, at real time or by repetitive iterations.
(d) Perform the above (b) and (c) in such a way that it will not deteriorate the work of the ventricle during systole but will decrease its energy consumption due to the decrease in the preload (End diastolic ventricle volume).
(e) Perform the above (b) and (c) so that most of the added external work will turn into work done on the blood.
(f) Perform (b) and (c) in such a way that it will improve the ventricle compliance and coronary perfusion, during diastole, by decreasing the ventricle diastolic pressure and increasing the aortic perfusion pressure.

The mode of operation and the significance of the appropriate timing and function of inflow, for obtaining the desired mechanical function of the heart are described below:.

Systolic Function

1. The external power generated by a normal heart, when the systolic pressure is 120 mm Hg, ejected volume is 70 ml, and systolic duration is 0.2 sec, is only 5.5 watts (during systole).

2. To increase the ejected volume by 20 ml against a systolic pressure of 120 mm Hg, during the systole—the needed additional external power is only 1.6 watts.

3. Muscle shortening decreases the average force generated by the actin-myosin crossbridges (Xbs), the motor units of the muscle. Hence compression of the ventricle wall (as done by Direct Mechanical Ventricular Assistance) decreases the ability of the ventricle wall to generate pressure.

4. Ventricle wall expansion (stretching) during systole (eccentric work) deteriorates left ventricular (LV) function, as does small wall vibrations or vibration in the cavity pressure.

5. The decrease in muscle shortening increases the time over which the Xbs are at a strong force-generating state (increases the duty cycle of the force-generating motors). Hence the decrease in wall shortening increases the generated pressure and the time over which the ventricle can generate pressure.

6. The energy consumption by the sarcomere (the muscle contractile element) increases with the increase in the shortening velocity, at high activation (free calcium level).

Diastolic Function

7. Significant numbers of failing hearts (more than 50% at old age)—suffer from diastolic failure, i.e. failure in filling the left ventricle chamber due to the decrease in its ventricle compliance.

8. The decrease in the ventricle compliance at early diastole, and hence the decrease in the early filling phase is partially attributed to a decrease in the rate of muscle relaxation (impaired calcium dissociation from the regulatory proteins).

9. Muscle (ventricle) shortening during the relaxation period—causes rapid force decrease and deactivation and increases muscle (ventricle) compliance.

10. An improvement in ventricle loading conditions, and particularly the decrease in the preload (end diastolic ventricle volume) decrease muscle energy consumption and allows long-term muscle remodeling and significant restoration of the normal function (as in cases of ventricle remodeling after mitral valve replacement and after unloading by the ventricular-assist device).

Note that the above features of the physiological heart imply that the control of the inflow and the outflow through the cannula, and hence the loading conditions imposed on the ventricle cannot rely only on the electrical activity, aortic pressure or heart sound but should be based on ventricle mechanics, i.e. ventricle diameters/volume, wall motion (shortening) and wall strains and on the timing of ventricle outlet valve opening and closure.

This VAD is designed so that it will utilize the physiological features of the biological heart mechanics (specifically items #3, 4, 5, 9, 10—above).

1. The device consists of a single cannula that is inserted into the ventricle cavity. There is no need for a second cannula as in shunting (bypassing) VADs, since the blood is pulled and pushed back into the ventricle cavity.

2. The device consists of single artificial blood chamber denoted as a displacement chamber. The maximal volume of the displacement chamber is around 30 ml.

Figure 3:
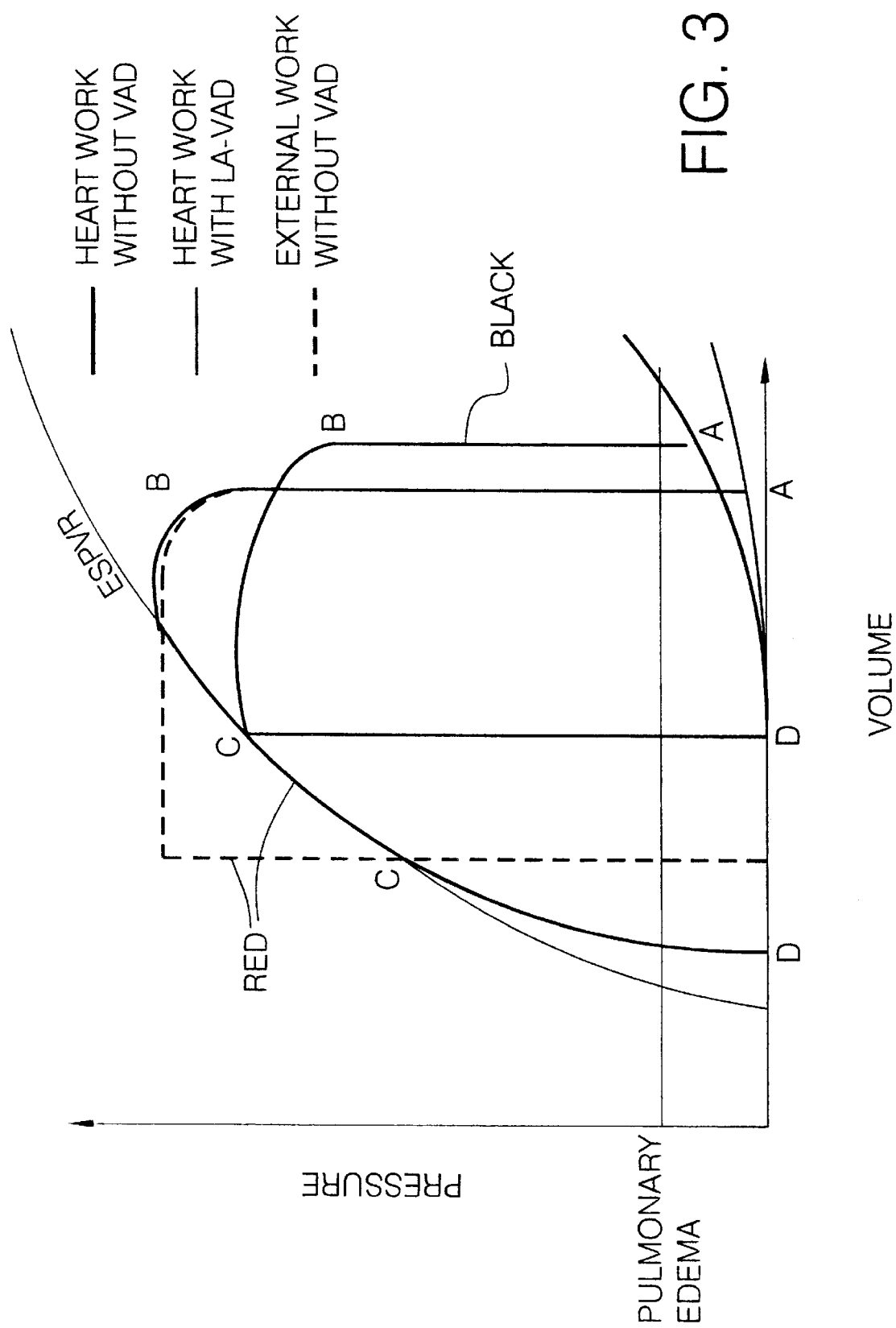
FIG. 3 is a pressure/volume graph illustrating the pressure-volume loops of a failing heart without and with the ventricular-assist device of the invention.

3. This VAD improves the systolic and diastolic functions and increases the external work done by the ventricle by changing the ventricle pressure-volume loops (FIG. 3). It provides the following advantages:

(a) Increases the pressure generated by the ventricle.
 (b) Increases the ejected volume.
 (c) Decreases the diastolic pressure (and hence improves the coronary perfusion).
 (d) Decreases the preload, the end diastolic volume and hence decreases the energy consumption.

4. The increase in the systolic pressure is achieved by decreasing the LV wall shortening (phase BC).

5. The increase in the ejected volume results from:

(a) An increase in the ventricle pressure.
 (b) Combined contribution of the blood inflow by the device and of the ventricle wall shortening.

6. The above is achieved by timing the blood inflow after the opening of the ventricle outlet valve or only after a detected shortening of a monitored region of the wall of the respective ventricle, to allow optimization of the cardiac output based on the mechanical function of the residual functional myocardium.

7. The device improves the ventricle diastolic function and ventricle filling by:

(a) Producing rapid emptying of the ventricle (phases CDA in FIG. 3) and decreasing the ventricle volume.
 (b) Increasing the ventricle wall compliance, due to the imposed ventricle wall shortening during the early relaxation phase (phase CD).

8. The blood outflow through the cannula should start after the closure of the ventricle outlet valve, and as early as possible during the isovolumetric relaxation phase.

9. The LV diameters, epicardial strains or ventricle volume are monitored in order to regulate the profile of the blood inflow through the cannula, to avoid ventricle stretching (eccentric work).

The average external mechanical power (P) needed in order to increase the cardiac output ($\Delta CO$) by half a liter per minute while the systolic pressure ($P_{SYS}$) is about 120 mm Hg is only 0.14 watts. Since:

$$P = 1/456 \cdot \Delta CO \cdot P_{SYS} \quad \text{(watts)}$$

where $P_{SYS}$ is measured in [mmHg] and $\Delta CO$ in [liter/min].

Consequently, from heat and energy considerations, a device with reasonable electromechanical efficiency can be implanted intrathoracic, and energized by an implanted battery.

In FIG. 3, the pressure volume loop of the failing heart has been shown in thicker lines with the ventricular-assist device and with a thinner line without the ventricular-assist device. The loops represent the work done by the ventricle and there is an additional increase in the external work done on the blood when the assist device is working as represented by the broken line.

Figure 4:
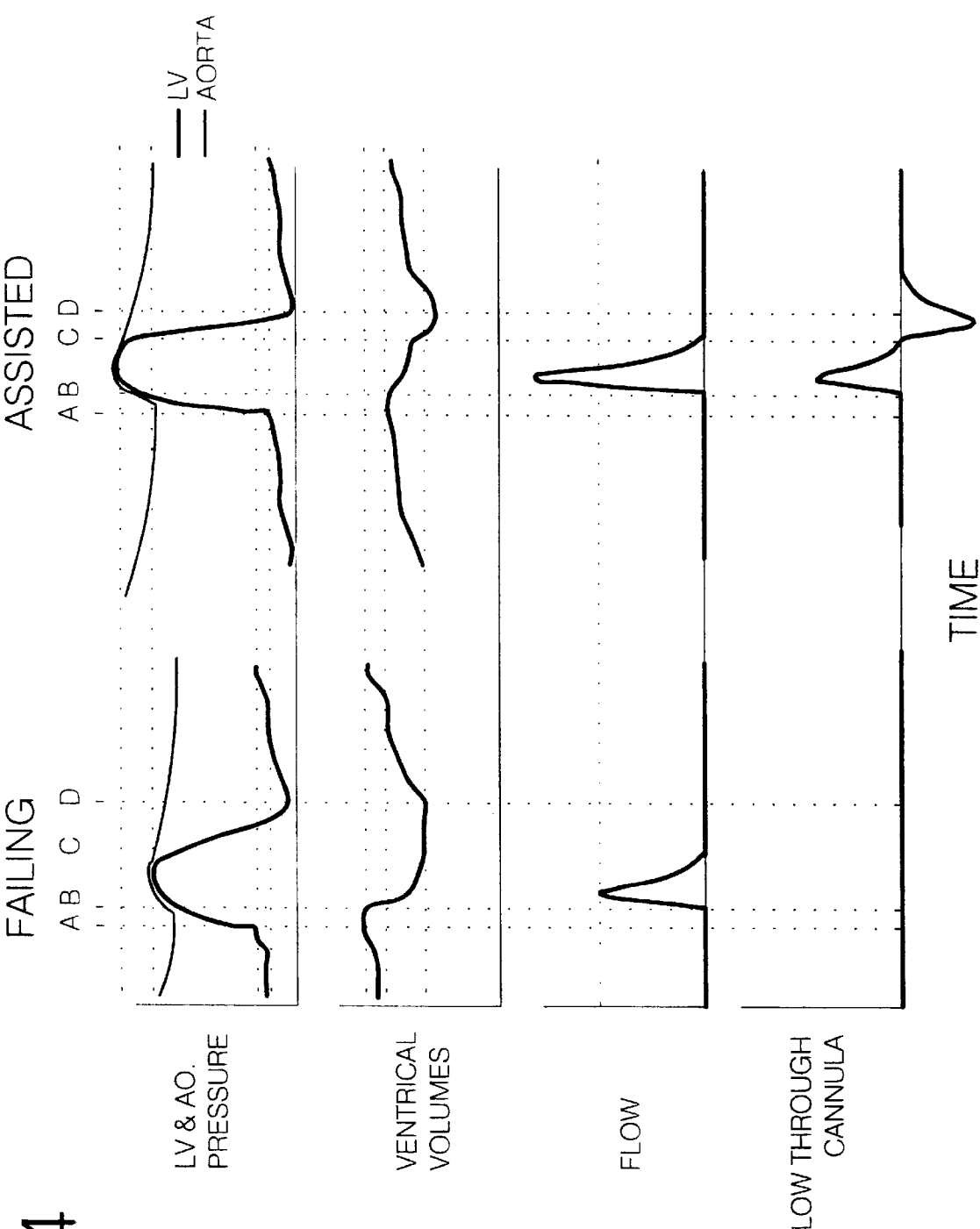
FIG. 4 is a diagram showing the time course of blood inflow and outflow into and from the ventricle cavity and it effects on cardiac mechanics: ventricle pressure, volume and the cardiac outflow.

FIG. 4 shows the effects of the forced inflow and outflow on the failing ventricle mechanics: ventricle and aortic pressure (Upper trace), ventricle volume (second trace) and the ventricle outlet flow (third trace) while the lower trace presents the time course of blood displacement, i.e. the blood inflow and outflow. The figure presents ventricle function without (left side) and with the assist device (right). Note the expected increase in the ventricle outlet flow, the increase in the ventricle and aortic systolic pressure, a decrease in ventricle shortening and the decrease in the end-diastolic volume.

Figure 2:
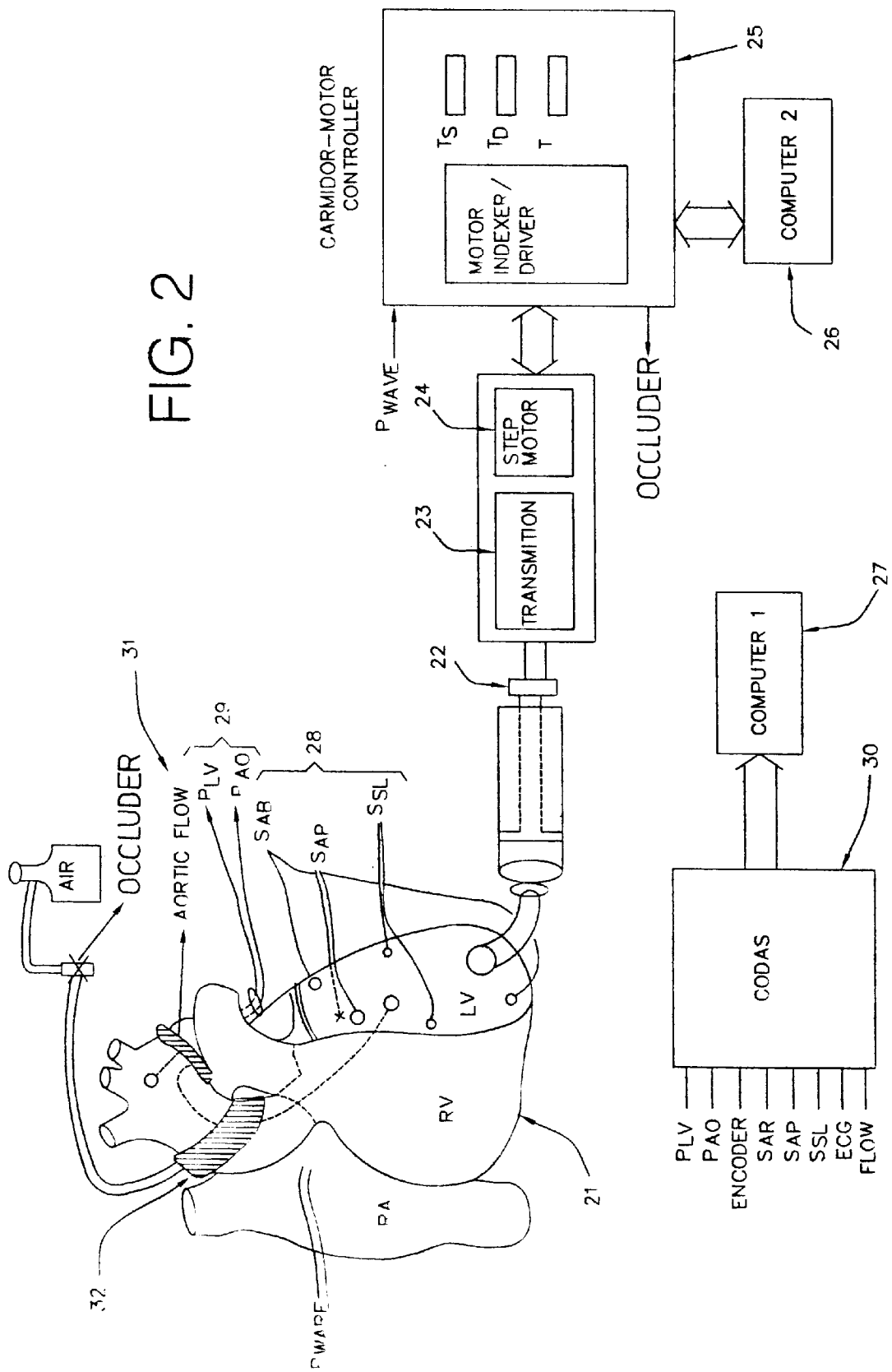
FIG. 2 is a diagram of an apparatus as used in the feasibility study of the invention, applied to pigs.

FIG. 2 shows the setup with respect to a heart in a feasibility study but is applicable to an embodiment applied to a failing heart with the exception that fewer sensors are required. The heart is represented at 21 and the right atrium is labeled at the right ventricle at RV and the left ventricle at LV. A cannula 14 is inserted into the ventricle cavity and is connected to the displacement chamber 19 driven by the transmission 23 from a stepping motor 24 of a motor controller 25 operated by the computer 26, i.e. the motor-control computer. A computer 27 analyzes the data from the sonomicrometers (ultrasound crystals) 28, pressure transducers 29 and flow meter 31. The position of the displacement chamber 19 is detected by the encoder 22 and represents the volume of blood ejected into the ventricle. Data acquisition system 30 is used to sample the sensors and transducers that are fed into the computer 27.

Figure 5:
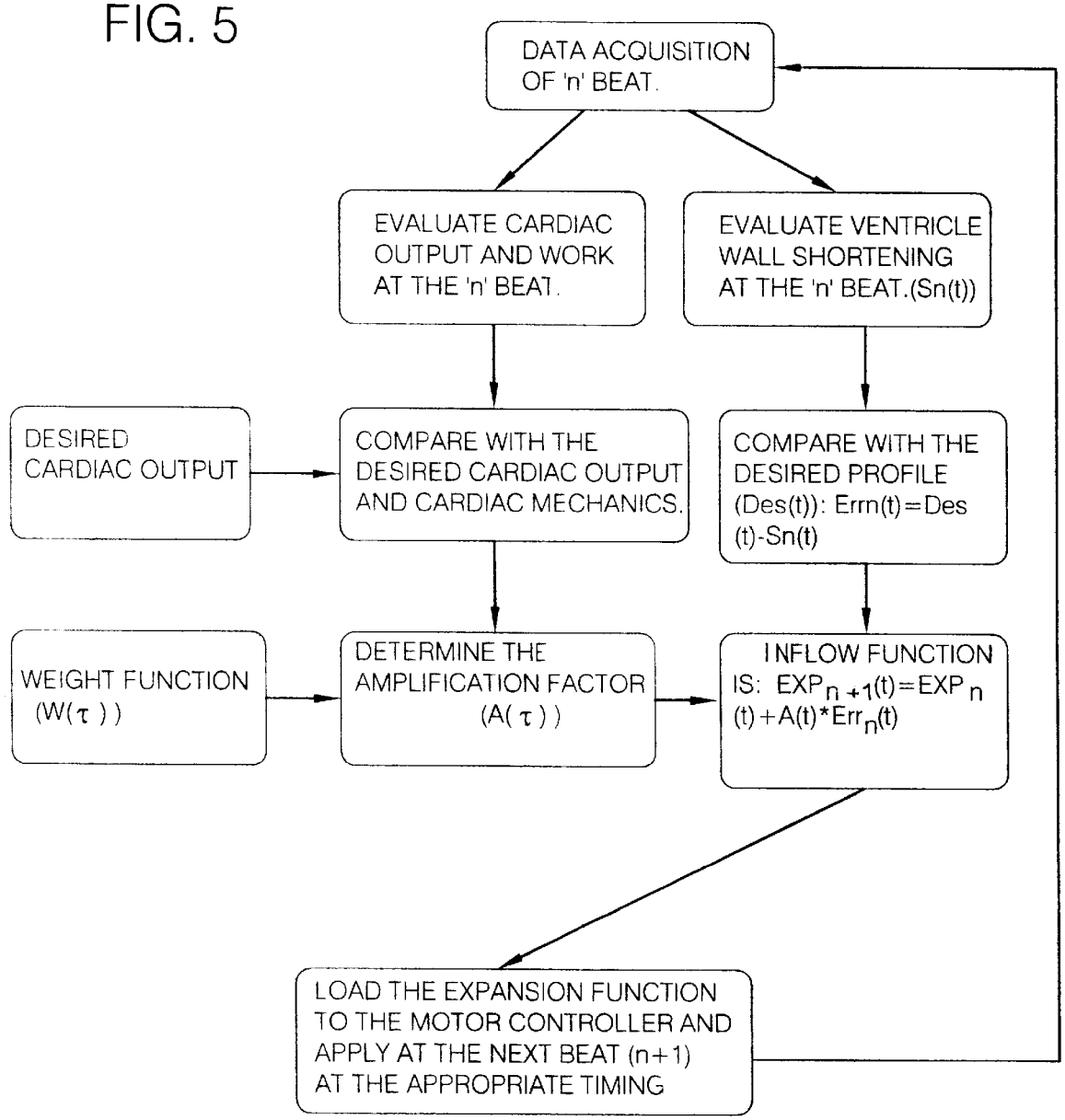
FIG. 5 is a flow diagram of one algorithm for the automatic regulation of the inflow of blood based upon monitoring the ventricle wall motion (shortening)
Figure 6:
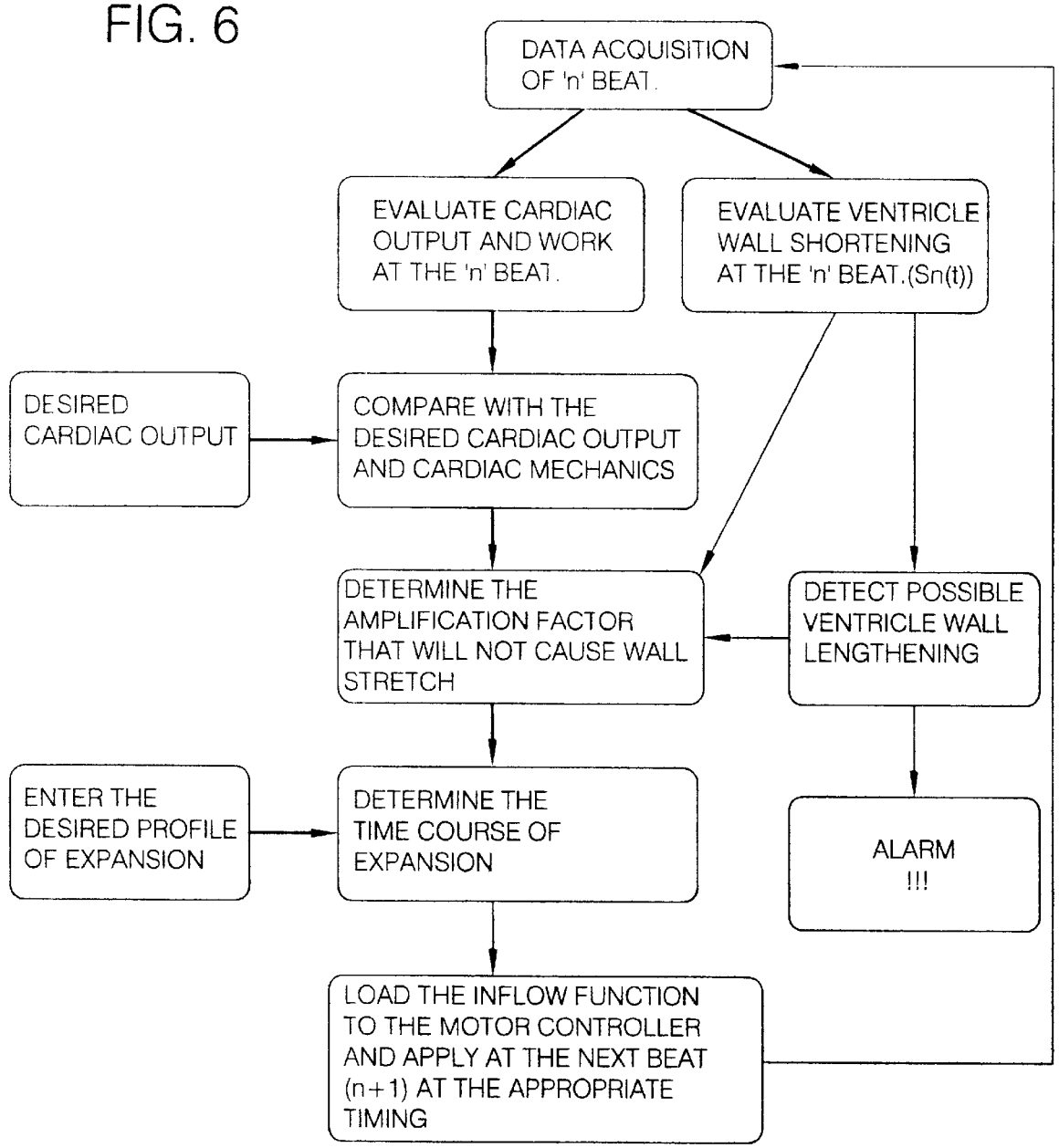
FIG. 6 is a similar diagram for a semiautomatic mode of operation.

Algorithms for controlling the profile of expansion of the ventricular chamber have been shown in FIGS. 5 and 6. FIG. 5, in particular, represents a flow chart for an automatic mode of regulation of the inflow profile, which is determined by monitored ventricle wall mechanics.

FIG. 6 is a flow chart for regulating the inflow where a profile of the flow is determined manually but in conjunction with continuous control so that the ventricle wall function will not deteriorate.

The device improves the ventricle wall capability to sustain elevated pressure. The injected blood into the ventricle cavity (inflow) aims not just to push blood out of the ventricle but also to elevate the pressure generated inside the ventricle cavity, which is maintained by the ventricle wall. To increase the ventricle ejected blood volume it is required to increase the pressure inside the ventricle cavity at any given impedance of the circulatory system, since the cardiac outflow is determined by the intraventricular pressure and the peripheral circulatory impedance. The maximal pressure that the ventricle wall can generate is obtained when the ventricle does not shorten. Ventricle wall shortening decreases the generated pressure (which relates mainly to the phenomena denoted as the force-velocity relationship). Therefore, the blood inflow through the cannula diminishes the ventricle wall shortening, which allows increase of the ventricle wall stresses and the generated ventricle pressure. Consequently, part of the inflow is used to compensate for the diminished ventricle wall shortening, while the rest is added to the ventricle outflow.

However, the inflow rate is limited so that it will not cause ventricle wall stretching. Stretching the muscle before the electrical stimulation or during the contraction (eccentric work) damages the cytoskeleton of the muscle, causes programmed cell death (apoptosis) and consequently leads to gradual deterioration of the muscle ability to generate force and to the increase in the resting force or stiffness. Consequently, inappropriate control of the timing or of the inflow profile leads to reduction of the generated pressure during the systole and impaired filling of the ventricle during diastole.

To increase the generated pressure, the blood inflow through the cannula is controlled so that the ventricle shortening will decrease. This can be done in real time, when the measurements of the ventricle wall motion are inversely fed back to the actuator controller, or by beat-to-beat regulation (see FIGS. 5 and 6). In the beat-to-beat iterative regulation the parameters of ventricle shortening are inversely fed into the actuator controller after multiplication by an amplification factor ($A_F$) (FIG. 5). This diminishes ventricle wall shortening. However, the exact effect cannot be predicted since the ventricle wall function is complex (nonlinear), time varying and spatially inhomogeneous. Therefore, the algorithm is based on successive iterations, which gradually decrease the ventricle wall shortening. This allows higher cavity pressure while the added cardiac output is provided by the inflow from the displacement chamber (FIG. 5). The obtained measured parameters during the next beat are fed (inversely and after amplification/attenuation) again and are used to correct the first approximated profile of the blood inflow profile. After few iterations (within 10 heart beats or within about 10 seconds) the desired inflow profiled is achieved.

This method allows continuous modification of the inflow profile function at almost real time, during its long-term operation, at various heart rate and physical activities (that change the loading condition imposed on the heart).

The beat-by-beat adaptive control is the preferred mode of operation (over the real time method) since it is fast enough (correction within a few beats) and it prevents high frequency oscillation. The real time method, where the inflow profile is determined within a single beat carries the hazard of causing fluctuation in the inflow, which will deteriorate the ventricle wall function. (The ventricle wall is sensitive to oscillation/vibration in the loading conditions).

In most practical expected operations the device will not operate at maximal power and the inflow will only partially diminish ventricular shortening. The aim is to add the minimal required external work that will allow substantial improvement of the quality of life. Note that normal cardiac output is about 2.5 to 3.8 liter/min/mm$^2$ while cardiac output of less than 1.8–2 liter/min/mm$^2$ is incompatible with life and causes organ hypo-perfusion and death. (An aortic balloon provides less than 0.5 liter/min—and provides adequate support in most (85%) cases of the postoperative cardiogenic shock). Similarly, we provide that the device should give an additional 1 to 2 liter/min, i.e. about 15–30 ml per beat. It is not desired to work at full actuator power since under this condition the ventricle shortening is minimal and while it may provide high cavity pressure, it does not ensure maximal cardiac output. The cardiac output is the sum of the inflow through the cannula and the ventricle wall shortening. An increases in the inflow may decrease the contribution of the ventricle wall contraction. Therefore the exact magnitude of the inflow is determined by the desired cardiac output. The parameters of the inflow that are under control are:

a. The inflow onset time.
 b. The inflow profile (initial and late flow rate).
 c. The total volume displaced.
 d. Timing the end of inward ejection (inflow).

Onset time of the inflow: The onset time of blood ejection into the ventricle cavity is defined by the time onset of significant ventricular wall shortening of the monitored portion of the ventricle wall. For a homogeneous ventricular wall—the onset time is determined by the opening of the ventricle outlet valve. For an inhomogeneous ventricle wall structure, as in a case of ventricle aneurysm (where part of the cardiac muscle has died and has been replaced by a fibrotic tissue) the inflow onset time may be determined by the performance of the preserved myocardium (cardiac wall tissue). The contraction of the preserved myocardium and pressure generation causes bulging out of the aneurysmatic (fibrotic) and dysfunctional portion of the ventricle wall. Hence, the residual preserved myocardium is doing work on the dysfunctional aneurysmatic wall, consequently, the cardiac output is reduced. In this case the blood inflow from the device can start before the opening of the ventricle outlet valve, in order to compensate for the dilatation and bulging out of the dysfunctional region of the ventricle wall. To enable this, the onset time of expansion is determined by monitoring the shortening of the preserved functional region of ventricle (the region of interest) and some of the sensors of the device are placed at the region of interest or monitor the motion of that region. (The sensors are described below). Therefore, the onset time may be determined by global parameters as the opening of the outlet valve and by regional parameters.

The end of inward blood displacement can be determined by cessation of ventricle shortening at a monitored region of interest or the detection of the occlusion of the ventricle outlet valve. Both are determined by appropriate sensors.

The inflow rate and the time course of blood displacement may be determined explicitly by the algorithm defined in FIG. 5. However, there is some flexibility that allows modulation of the inflow time profile by making the amplification factor ($A_F$) a function of time ($A_F(t)$) and not a constant. The amplification factor ($A_F$) is multiplied at each iteration (beat) by the weighting function (W(t)) that is determined by the operator, based on empirical observation (see below) and allows changing the magnitude of the feedback loop within the systole. ($0 \leq W(t) \leq 1$, where t varies between the inflow onset time (0) and the end of systole, or the closure of the ventricle outlet valve (T), $0 \leq t \leq T$). The default mode of operation is with a constant weighting function (W(t)=1). However, the weighting function allows optimization of the device function based on the following idea: The rate of blood ejection from the normal and failing ventricle is a maximum at the beginning of the ejection phase, just immediately after the opening of the ventricle outlet valve. Consequently, the main contribution of the ventricle shortening to the cardiac output is obtained at an early phase of ejection. The higher amplification factor at the early phase of ejection will diminish the contribution of the ventricle wall shortening to the cardiac output but will increase the cavity pressure. A higher amplification factor at the last phase of ejection allows the elongation of the duration of the ejection phase by allowing the ventricle wall to sustain pressure for a longer time. Hence, the weighting function allows regulation of:

1. The contribution of the ventricle wall to the cardiac output;
 2. The maximal cavity pressure;
 3. The duration of the ejection phase.

Moreover, the weighting function may be used for weaning the patient from the device. Decreasing the magnitude of the feedback loop at the early phase of ejection, i.e. decreasing the weighting function at the early phase of ventricle ejection (W(t)=0 as t approaches 0), increases the contribution of the ventricle wall shortening to the cardiac output. The weighting function allows modulation of the work of the failing heart and allows gradual adaptation of the failing heart to normal loading conditions. It is expected that there will be a gradual decrease in the failing heart diameter when the assist device is working. Therefore, it is expected that the device will allow gradual decrease in the heart diameter and gradual recovery of its function. Hence, the device can be used as a "bridge to recovery" both for acute and chronic heart failure, so that after the period of assisted circulation, it will be possible to remove the device without the need for cardiac transplantation. In that case, the heart has to be gradually accommodated to the prevailing loading condition without the device and the assistance of the device should be gradually attenuated.

The blood inflow rate is increased until the desired cardiac output is reached or until a limiting parameter is achieved. The limiting parameter is the detection of ventricular wall stretch.

The profiles of the inflow and outflow are continuously evaluated based on the obtained pressure, flow, ventricle volume and ventricle diameter changes, so that the parameters of the flow (velocity, acceleration) are under continuous adaptive control.

Figure 7:
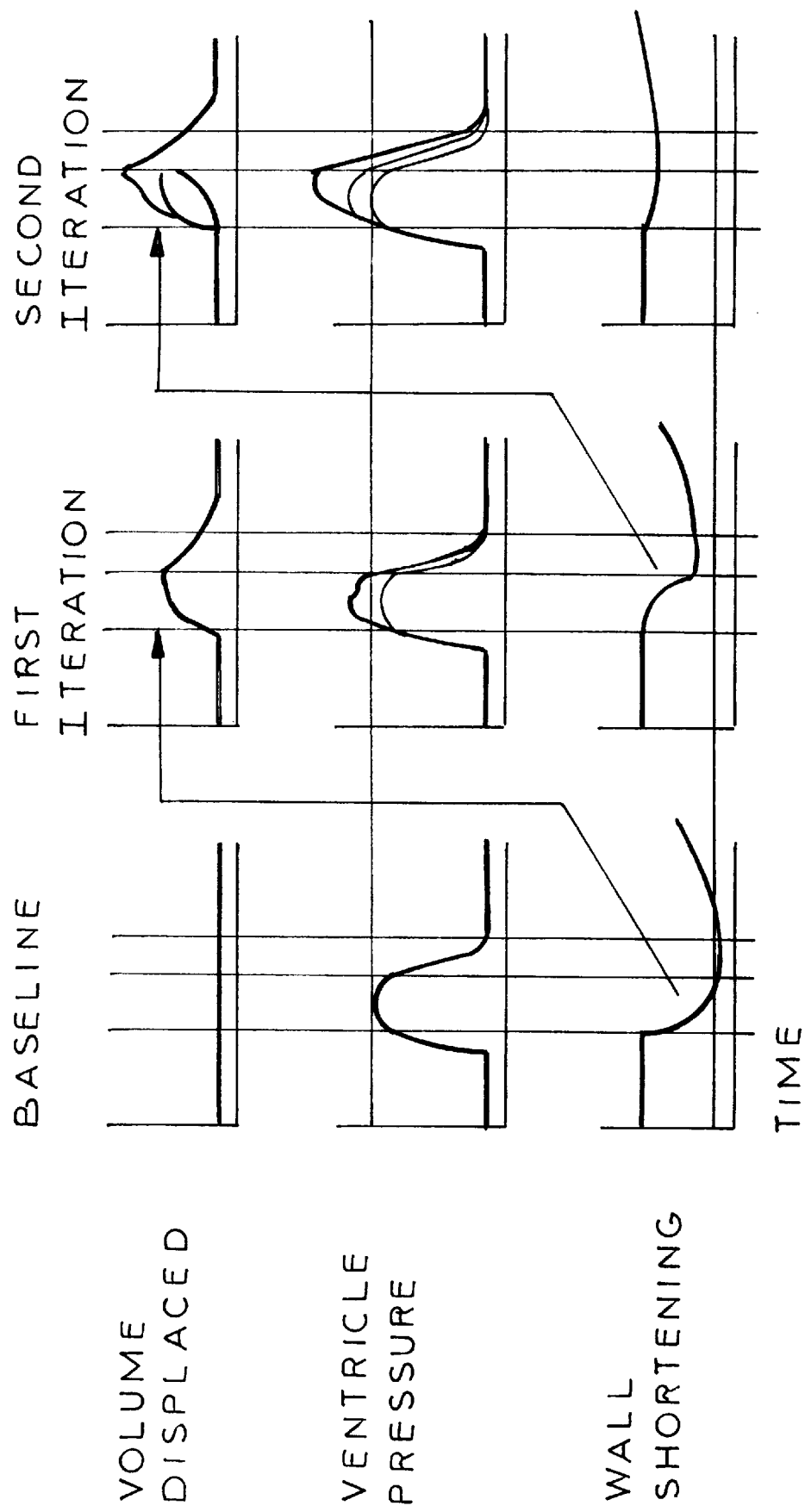
FIG. 7 is a diagram explaining the operation of the invention, in the iterative mode of controlling the inflow function.

The algorithm of either FIG. 5 or FIG. 6 provides monitoring of at least one parameter of ventricle motion to prevent ventricular stretching during the inward blood ejection (inflow) phase. As soon as wall stretching is detected, the inverted function is added to the last function of the inflow profile and is eliminated in the successive beats. (See also FIGS. 5 and 7). Moreover, the device works far from maximal power and thus far from the limits of ventricle wall motion where wall stretching may appear, so that some wall shortening will always remain. This ensures the safety of the device.

Ventricle wall lengthening can trigger an alarm and the amplification factor ($A_F$) at the next beat is reduced to a provisional used value or by a certain percentage whereupon operation can continue without danger. The end of inward blood ejection in this embodiment is determined by the earlier of a time set by the operator and closing of the ventricle outlet valve.

The algorithm allows operator intervention. In the algorithm of FIG. 6, the operator can determine the exact profile of the inflow function. The inward displacement may be an exponential function or a ramp function or any other function of time, including polynomial functions. The operator, therefore, determines the profile of the inflow, however the magnitude is determined based upon beat-to-beat analysis of the ventricle wall shortening. The iterations are repeated until the desired cardiac output is reached or till ventricle wall shortening diminishes to a point that a further increase in the inflow rate might cause ventricle wall stretching.

According to the invention the outflow through the cannula is initiated after the closure of the ventricle outlet valve, but while the pressure in the ventricle wall is still high (isovolumetric relaxation phase) in order to impose ventricle wall shortening and deactivation. Rapid wall shortening during the relaxation phase leads to rapid deactivation of the cardiac muscle and increased ventricle compliance. The outflow through the cannula expedites opening of the ventricle inlet valve, faster ventricle refilling and faster decompression of intramyocardial pressure, which improves the coronary flow.

The parameters of the outflow are: outflow onset time, outflow rate and total outflow volume. The outflow time onset is triggered by the detection of the ventricle outlet valve closure, which reflects the end of ejection. Earlier outflow diminishes the cardiac output, while outflow that are initiated late in the relaxation phase have less effect on the rate of wall relaxation (ventricle compliance). The timing of the outflow is under real time control, based on the measurements previously described.

There are upper and lower limits to the outflow. The maximal velocity of muscle shortening is reached when the muscle is unloaded (shortening against zero load). The maximal rate of cardiac muscle shortening is around 6 muscle-lengths per second, and is limited by the inherent properties of the cardiac motor units—the crossbridges. Imposing a shortening rate above the maximal unloaded velocity causes only muscle buckling. The maximal rate of deactivation is achieved when the ventricle wall shortening is close to the maximal rate of cardiac muscle shortening. Consequently, practically the outflow velocity should be near the upper limiting ventricle shortening rate so that it will cause maximal ventricle wall deactivation.

The simplest way to produce the rapid shortening is to expose the displacement chamber and consequently the ventricle cavity (through the cannula) to the near zero intra-thoracic pressure. Exposing the high ventricle cavity pressure (above 60 mm Hg) to the near zero pressure, will produce the power for the outflow during the diastole, without the need of additional external power supply, i.e. "passive" retraction of the displacement chamber. Active retraction of the displacement chamber is required only when there is significant resistance to the blood through the cannula.

The lower outflow rate is limited by the duration of the diastolic period and is determined by the heart rate. The outflow profile is terminated before each cardiac cycle. The total blood volume displaced is controlled to be equal to the volume of blood ejection into the ventricle, so that the displacement chamber works in a repeatable cyclic mode and the inflow volume is equal to the outflow volume.

Note that no tight control of the outflow profile is required, since there is no evidence that rapid shortening can damage the ventricle wall integrity. Consequently, the outflow profile can be as simple as possible, as a trapezoid function of time (acceleration, constant velocity of contraction, deceleration).

The detection of the inflow and outflow onset time is done in real time (time response of few milliseconds) by utilizing at least one of the following data acquisitions of cardiac mechanics, that allows determination of whether the ventricle outlet valve is open or closed:

a. The ventricle pressure and the aortic pressure, or the gradient between the two.

b. The ventricle outlet flow, which can be measured by a flow meter (as an ultrasonic or electromagnetic flow meter) or by utilizing the Doppler effect.

c. The ventricle volume—by ultrasound or electrical impedance measurements (impedance catheter).

d. The ventricle diameters, as for example by ultrasonic sonocrystals.

e. Ventricle wall shortening—as by strain gauges.

f. The ventricle pressure and any of the above indexes of wall motion, as the Ventricle Volume, the ventricle flow, diameters or strain. This allows plotting the pressure-volume or strain loops (as FIG. 9) and to define the onset times.

g. Heart valve sounds—that reflects the closure of the outlet valve.

Note that the electrical activity of the myocardium (ECG) may also be used. However, it is not considered as a precise means for determining the time course of cardiac mechanics.

The inflow onset time can precede the opening of the ventricle outlet valve when there is cardiac wall inhomogeneity (as in case of cardiac aneurysm—a scar tissue that may bulge out during the systole). In that case, the inflow can be optimized based on the mechanical function of the preserved functional ventricle wall (myocardium). Consequently, the timing and the inflow profile are determined also based on regional mechanical parameters, as ventricle diameters or distance between anatomical points (markers) on the ventricle wall, or between ultrasonic sonocrystals, or local measurements of ventricle wall shortening as by strain gauges.

The device may be implanted near the heart (for acute or chronic heart failure) or placed near the chest for a short period of assist (bridge to recovery) and the total blood volume in the displacement chamber and the cannula is relatively small (around 30 cc). Consequently, the kinetic energy spent for the fluid flow is negligible, and the mechanical time delays are in the order of milliseconds.

The displacement chamber can be a simple syringe type, where the position of the piston of the syringe is computer-controlled, a computer-controlled bellows (pneumatic or hydraulic) or a flexible diaphragm.

The actuator for the displacement chamber may be of various types, but should be able to allow high speed of operation (in the order of linear motion of 400 mm/sec), and should have low energy consumption and high efficiency, to reduce the heat dissipation and to allow implantation. The actuator can be any electrical motor, e.g. a direct-current linear motor, a voice coil or a centrifugal or axial flow pump. The actuator can also be a transplanted heart, from human or animal source (pig). The advantage of this mode of heart transplantation, where the implanted heart is used as the motor that assists the natural failing heart, and does not replace it, are that a) The motor is very efficient and economical and there is no need for power supply (except for the control unit and for the pacemaker, b) The natural heart is not taken out, and will always remain in place, eliminating the problem of rejection of the implanted heart (there is always some residual function of the native heart and the implanted heart can be replaced in case of need (rejection).

c) The operation procedure is simpler compared to regular heart transplantation.

The displacement chamber is inserted into the implanted heart through the inlet or outlet valve orifices of the implanted heart. The coronary circulation of the implanted heart is connected to one of the patient's arteries.

The actuator can also be a patient's own skeletal muscle that is wrapped around the displacement chamber.

MAJOR ADVANTAGES OF THE INVENTION

1. It is a simple mechanical device with only one cannula, hence, simple minimal invasive surgical procedure is required for the implantation of the device (compared to the complex surgery required with the shunting VADS). This reduces the duration and risk of the operation, and shorten the postoperative recovery period.

2. It is based on the physiological control of cardiac muscle contraction, and allows optimization of the physiological heart function. The residual mechanical function of the heart is utilized, so that the required additional external work is minimized (i.e. smaller device, smaller energy consumption).

3. It generates smaller forces, about tenths of needed forces in the direct mechanical ventricular actuation, i.e. smaller device, smaller energy consumption.

4. It improves the systolic function of the failing heart by increasing the stroke volume, the systolic pressure and the stroke work.

5. It improves the diastolic function of the failing heart by decreasing the end diastolic pressure and by forcing rapid deactivation of the ventricle wall early in the diastole, which increases the ventricle compliance.

6. No need for artificial valves since the blood is pushed back and forth through the same cannula (less thromboembolic complications).

7. It has a small surface area in contact with blood, (single cannula and small displacement chamber) and hence less thromboembolic complications.

8. The displacement in the blood displacement chamber and the flow in the cannula impose physiological shear stresses on the blood, due to the small blood volume that is pushed back and forth. This reduces the risk of hemolysis.

9. It preserves the physiological pulsatile flow for both the heart and the circulatory system.

10. It can be used as a bridge to recovery, since it impose physiological loading on the native ventricle wall, decreases the energy consumption (by reducing the preload) and improves the coronary flow, i.e. improves the balance between energy supply and demands.

The results of the method of the invention are:

1. Increase in the cardiac output—due to the combined effect of the device inflow and the cardiac wall shortening.

2. Increase in the systolic pressure—mainly since the device reduces cardiac shortening and the accompanied decreased ability to generate pressure.

3. Decrease in the end-diastolic volume, which relieves congestion, due to both the improved cardiac output and the increase in the ventricle wall compliance.

4. Decrease in the energy consumption of the heart and increase in cardiac efficiency, due to the decrease in the end-diastolic volume and the increase in the generated external work (including the shortening during the diastole), as shown in FIG. 4.

5. Slow remodeling of the ventricle geometry and gradual decrease in the ventricle size, due to the decrease in the end-diastolic volume and the decrease in energy consumption. This may provide the basis for using the device as a bridge to recovery and not only as a bridge to transplantation.

Figure 8:
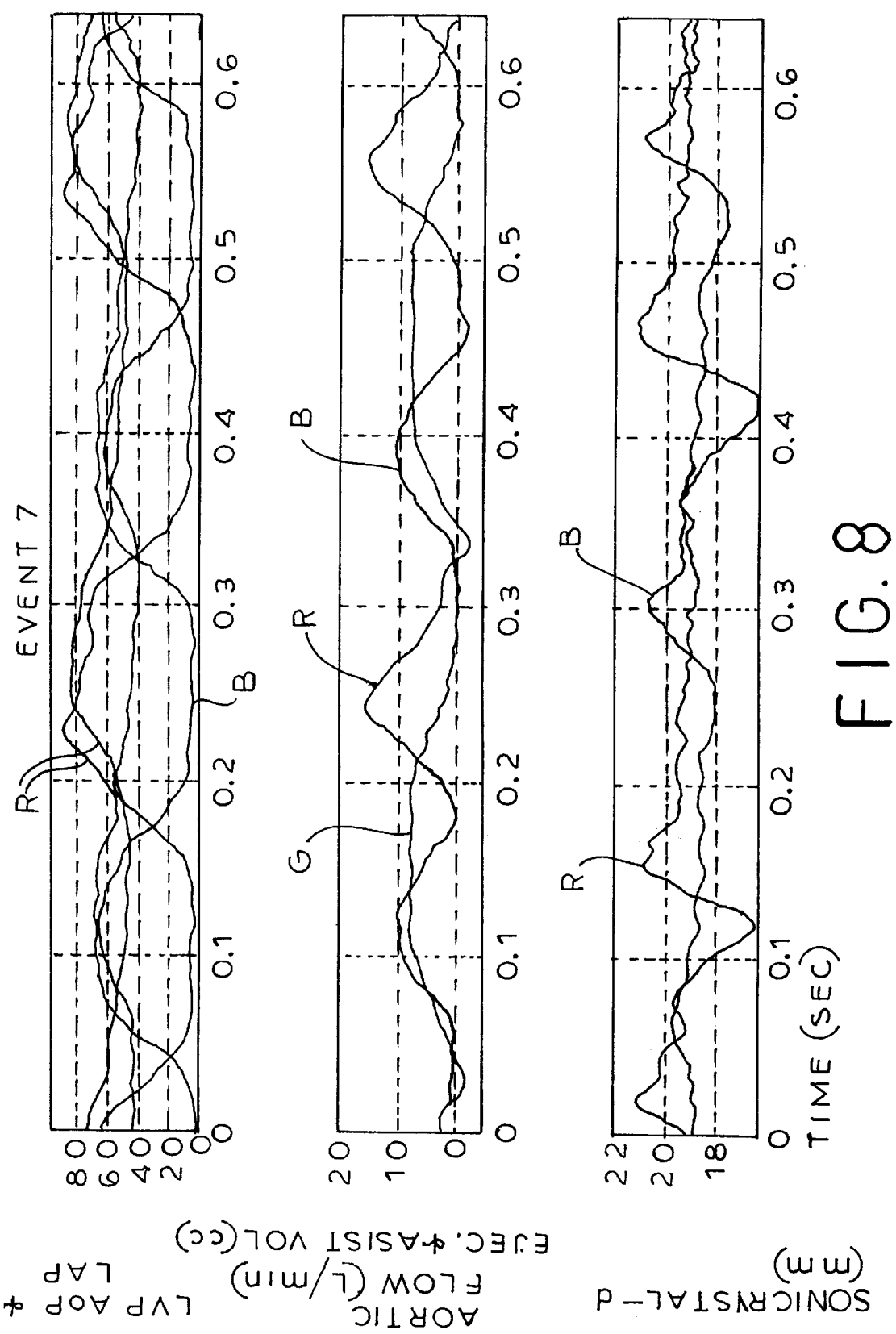
FIG. 8 represents results from experimental feasibility studies, where the device was used to assist the failing left ventricle, in an acute heart failure induced by coronary ligation.
Figure 9:
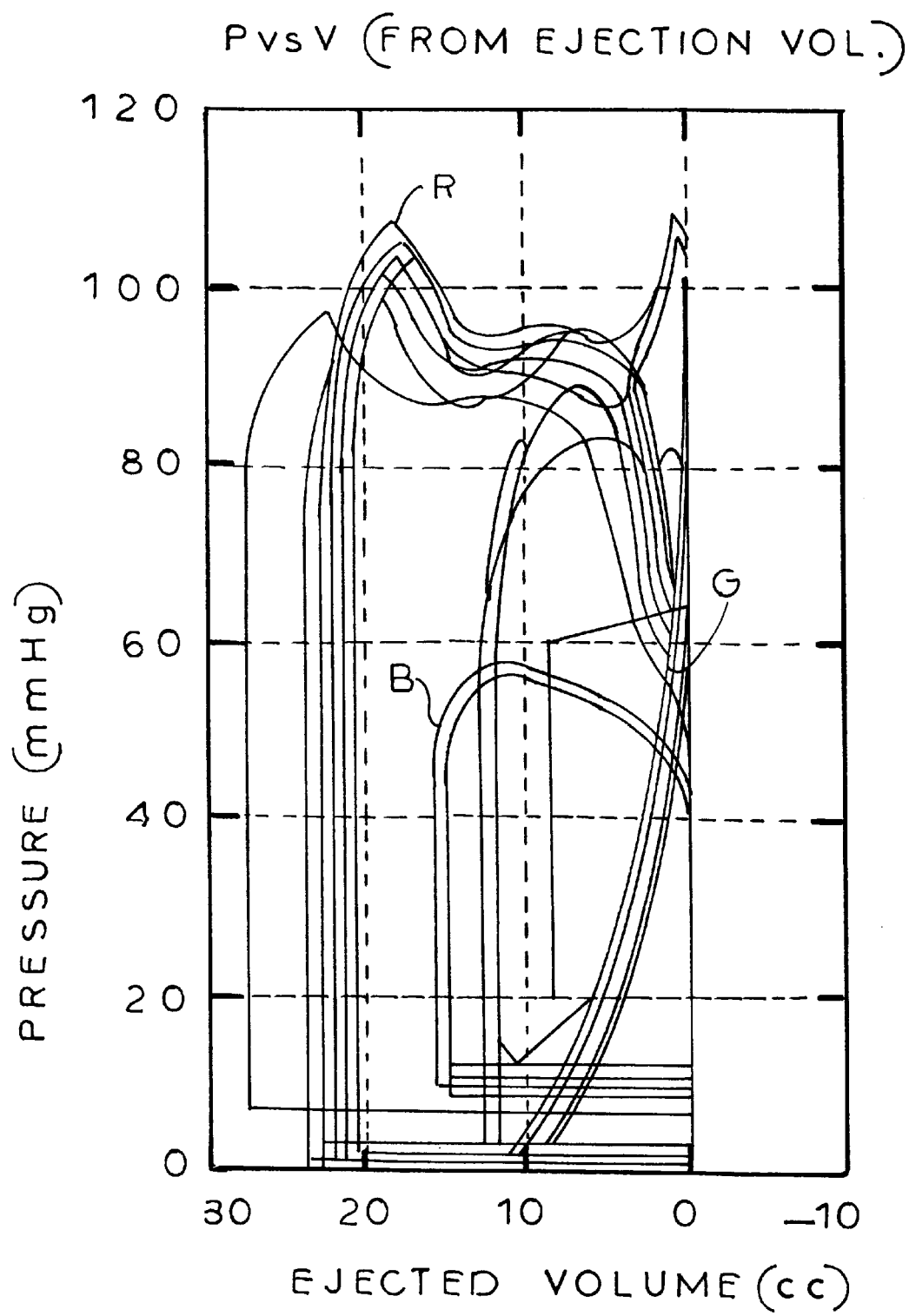
FIG. 9 is a diagram illustrating the external work done by the failing heart with and without the assist device.
Figure 10:
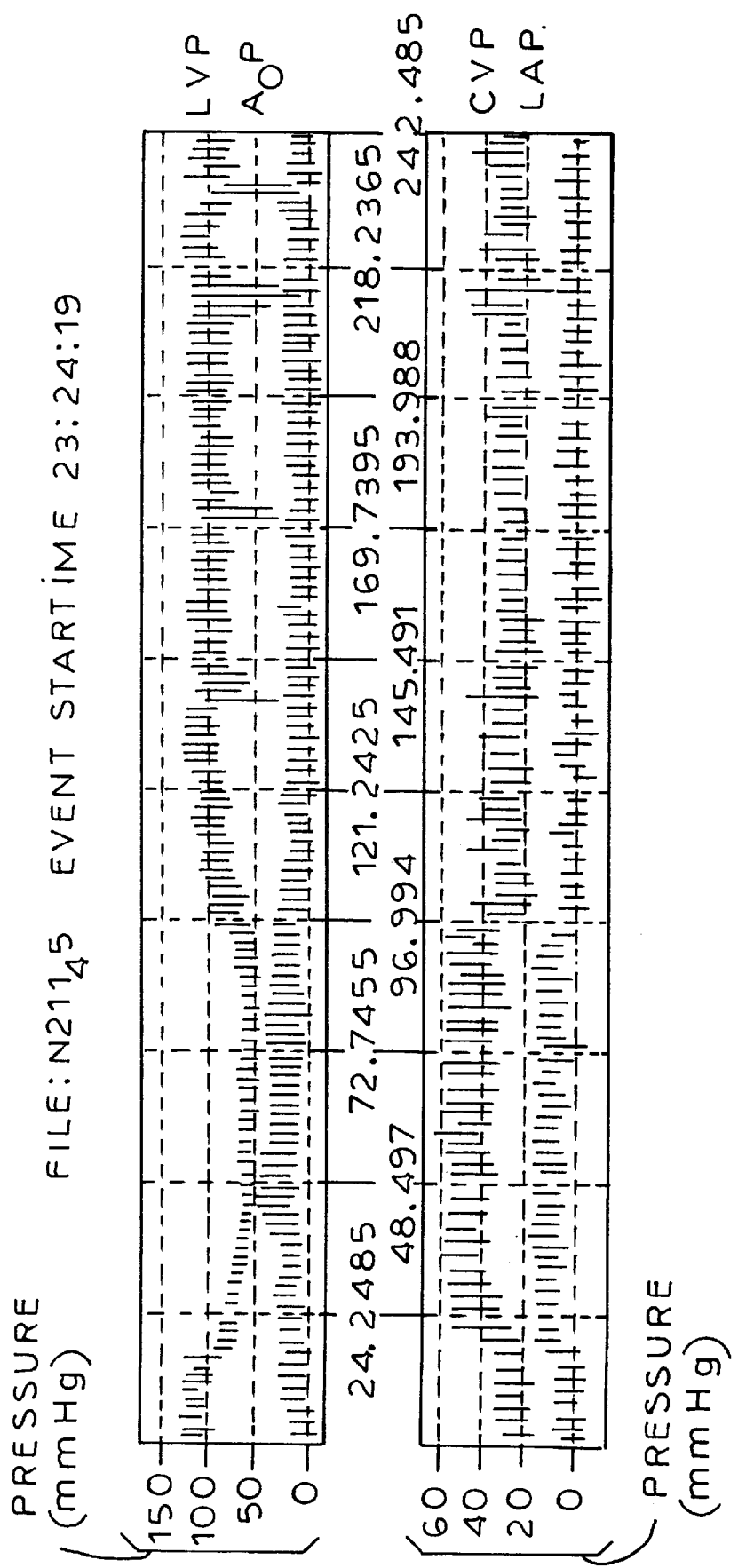
FIG. 10 is a diagram presenting the advantages and efficacy of the assist device in the treatment of severe heart failure in the form of a set of graphs illustrating ventricle pressure, aortic pressure, and aortic flow during assist and for a period that the assist device was stopped. Note that the assist device brought the blood pressure and the cardiac output into the normal range, while the pressure and flow dropped down to value that are incompatible with life when the assist was stopped.
Figure 10:
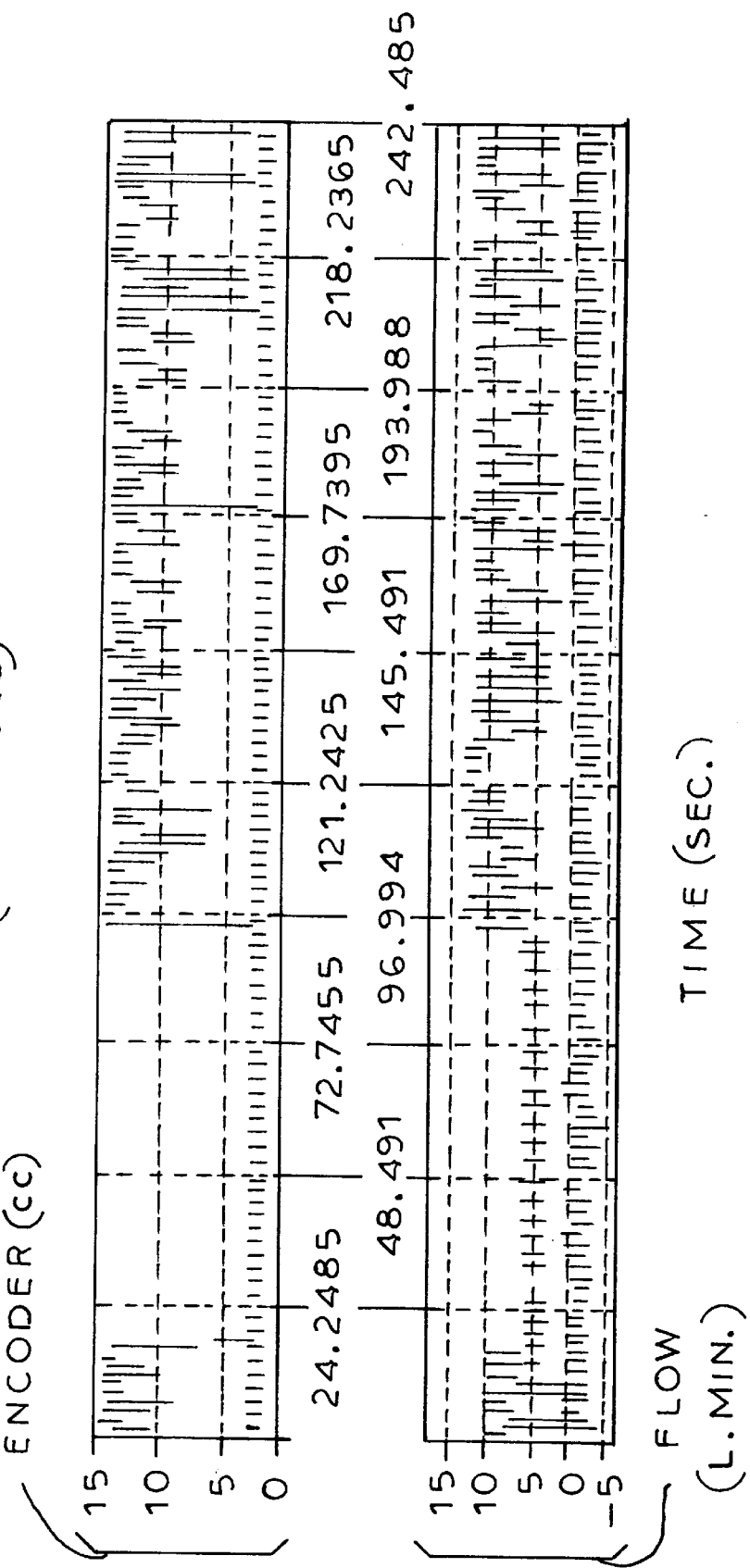

All of these advantages have been demonstrated, as shown in FIGS. 8, 9 and 10.

The cannula is inserted into the ventricle cavity through the ventricle wall, after exposing the ventricle by left thoracotomy. The device is introduced through the ventricle apex, when the heart failure is due to dilated cardiomyopathy or other diseases that cause homogeneous dysfunction and decrease in the ventricle contractility. If there is segmental inhomogeneity, other locations for cannulation may be considered, also in combination with aneurysmectomy or partial ventriculectomy of the malfunctioning region. In general, the cannula can be implanted into the ventricle at any site of the wall that allows easy access and no interference with papillary muscle or ventricle valve apparatus or the cardiac circulatory or conductive systems. Hence, the surgical procedure is almost minimally invasive. Also, the implantation of the cannula into the ventricle cavity, through the apex, is widely used at the clinics and is required for the implantation of all the currently available VADs (Most of the cannulas are used for draining the ventricle, and are introduced through the apex).

A typical validation setup is shown in FIG. 2. An example of application of the invention to a pig model is given below.

The anesthesia of the pigs is maintained by Fentanyl (Beatryl) (10 $\mu$gr/kg/hour) with Pancuronioum (0.2 mg/Kg/ hour). Two millars transducers (pressure transducers) are used, one is inserted into the LV cavity and the second is placed in the aortic arch. The transducers can be inserted percutaneously through major arteries but a pressure gauge on the ventricular edge of the cannula can be used instead.

During the studies the heart was exposed by mid-line sternotomy and pericardiotomy. Normally, however, the device is implanted by a small thoracotomy that will expose the ventricle (apex), so that the cannula will be introduced into the ventricle cavity by a minimal invasive procedure. Alternatively the device may be inserted under an ultrasound or other imaging guided modality.

The cannula (inner diameter of 8 to 10 mm) is connected to the displacement chamber (FIG. 2).

The displacement chamber consists of a diaphragm (80 mm in diameter). A displacement of 1 cm of the diaphragm produce volume change of 30 ml. The diaphragm is displaced by an external motor. The motor (a Pacific scientific step-motor and controller were used for the feasibility study) dictates the rate of blood inflow and outflow. The profiles of the inflow and outflow (flow rates, duration and total volume) are determined by the programmable driver. These parameters are entered into the actuator driver between consecutive beats. Hence the computer-controlled system allows imposition of different volume changes and various profiles of volume changes. However, the inflow and outflow onset times are determined in real time, by a real time program (LabView has been used during the feasibility study). The timing of the inflow is synchronized with the ejection phase of contraction (as shown in FIG. 4). FIG. 8 presents the effect of the controlled volume displacement (the G trace at the second row) on the cardiac output, i.e. the aortic flow or the blood ejection into the aorta (second trace) and the generate pressure (top row). In this figure the measurements during assisted circulation (R) were overlain on the measurements during the normal contractions, without assist (B) of the failing heart. Note the marked increase in the generated pressure and in the aortic flow, and also the effect of the device on the ventricle volume, as presented by the monitoring the ventricle diameter (lower trace). Slight reduction in the ventricle shortening during systole (lower trace) allows to increase the generated pressure and to provide significant larger cardiac output.

The profile of volume displacement is determined before each cardiac cycle, and is not changed within the systole.

An occluder 32 (FIG. 2) is placed around the ascending aorta only during the feasibility study. This allows to evaluate the maximal pressure that can be generated by the heart.

The LV diameters are measured by sonomicrometers 28 (FIG. 2) (Sonometric Inc.), implanted into the LV wall. The sonomicrometers are used to measure precisely the ventricle diameter during the feasibility study. Three to six sonomicrometers are implanted and allow to measure up to 15 diameters that are used to reconstruct the ventricle geometry and volume. The sonomicrometers provide additional important information that allows verification that no stretch is imposed on the ventricle wall (no eccentric work).

The final device will include some detectors of the ventricle volume, as ultrasound crystals or conductance electrodes, which will allow the measurement of the dynamic changes in ventricle volume.

A flowmeter 31 (FIG. 2) is placed around the aortic arch to record the aortic flow in order to quantify the effect of the device on the cardiac output and it provides additional transducer for monitoring the onset time and the end of ejection.

The onset of the ejection phase and the closure of the ventricle outlet valve were detected during feasibility studies from:

1. The analysis of the relationship between the intraventricular pressure and the aortic pressure.
2. The changes in ventricle volume and diameters, measured by the sonocrystals or the conductance catheter.
3. The aortic flow.
4. The analysis of the intraventricular pressure-volume or the intraventricular pressure-strain relationships.

All of these measurements add further information for the precise determination of the trigger timing, during the feasibility study. However, only one of these methods is sufficient for the final device. The results presented here (FIGS. 8–10) are based on a trigger signal derived from the analysis of the pressure difference between the ventricle and the aorta. The sensors used: pressure transducer, ultrasound crystals (distance), Doppler measurement (flow) and conductance electrodes (volume) can all be attached to the cannula that is inserted into the ventricle cavity.

Eighteen experimental studies have been performed using 3-month old pigs (body weight of about 35 Kg) to validate the suggested method. Note the marked increase in the: stroke volume (the volume ejected at each heart beat), peak aortic flow and the ventricle and aortic pressure (FIGS. 8, 9, 10). Although we have used only small volume changes, of 8–10 ml (FIG. 9 G), a significant increase in the cardiac output is observed. The peak aortic flow increases by approximately 30 percent and the stroke volume increased by 6 ml per beat, i.e. by more than half a liter per minute for a pig with cardiac output of 2.5 l/min.

Moreover, the device has a significant stronger effect as the severity of the heart failure aggravates. The device increases the cardiac output of the failing heart from 1.3–1.5 to 2.3 l/min (more than 50%) and brings it almost to the normal cardiac output ranges.

FIG. 9 represents the work done by the heart during normal (B) and assisted (R) beats. The area inside the pressure-volume loops presents the generated external work. Note the marked increase in the peak systole pressure during the assisted beat (105 vs. 58 mm Hg), and the increase in the ejected volume (22 ml vs 15 ml). Moreover, the external work, the work done on the blood (which is described by the area inside the loops in FIG. 9) is more than doubled. This increase in the external work is due to the added work done by the assist device.

The advantages and efficacy of the assist device in the treatment of severe heart failure and cardiogenic shock are presented in FIG. 10. The diagrams illustrate ventricle and aortic pressure (upper trace), the left auricle pressure (second trace), and the aortic flow (lower trace) with and without the device. The time over which the device was working is shown in the third trace. While the assist device support the failing heart, the blood pressure and the flow were in the normal range. However, when the device was stopped (Note the third trace), the ventricle and the aortic pressure dropped down (from 120 mm Hg to 60 mm Hg), the cardiac output was markedly reduced (from 2 L/min to 1.2 L/min) and the left atrial pressure went up (from 15 mm Hg to 30 mm Hg), which may lead to pulmonary congestion and death. When the assist was resumed, all the parameters returned back to the normal range.

I claim:

1. A ventricular assist method that comprises the steps of:
   (a) inserting into at least one failing ventricular cavity of a failing heart through a wall thereof a respective cannula connected to a blood displacement chamber having a blood displacement actuator;

(b) in cadence with normal functioning of said failing heart, effecting blood inflow into the ventricle cavity from the displacement chamber, with each heart beat and commencing only after opening of an outlet valve of the respective ventricular cavity of the failing heart or only after detecting a shortening of a monitored region of a wall of the respective ventricular cavity of the failing heart and continuing during an ejection phase of the respective ventricular cavity, thereby augmenting ejection volume from the respective ventricular cavity by up to a maximum volume generated by the blood displacement actuator, per systolic phase;

(c) controlling a time course of blood inward displacement through the said cannula in step (b) thus reducing a shortening and thereby increasing a ventricle pressure in said ventricular cavity, but at the same time preventing stretching of a respective monitored ventricular wall region of the failing heart by comparison with ventricular wall shortening without an inflow from the chamber; and (d) retracting blood from said failing ventricular cavity, through the cannula immediately upon closing of a respective outlet valve of the failing ventricular cavity.

2. The method defined in claim 1, further comprising the steps of:

measuring parameters of ventricular wall motion during systole, the parameters comprising one of regional wall motion parameters, and global cardiac function parameters; and applying and controlling a profile of the blood inflow generated by the blood displacement actuator to decrease a measured ventricular wall motion, thereby obtaining an increase in pressure within the respective ventricular cavity and an increase in the cardiac output.

3. The method defined in claim 2 wherein said parameters include ventricular diameter.

4. The method defined in claim 2 wherein said global cardiac function parameters include ventricular volume.

5. The method defined in claim 2 wherein said regional wall motion parameters include ventricular wall strain.

6. The method defined in claim 2 wherein said global cardiac function parameters include ventricular flow.

7. The method defined in claim 2, further comprising inserting a respective cannula into each of the ventricles of the failing heart and connecting the respective cannula to a respective blood displacement chamber, blood flow in each of said cannulas being effected by respective actuators.

8. The method defined in claim 1, further comprising the steps of:

monitoring at least one parameter of ventricular wall shortening and at least one parameter of and ventricular output of said ventricular cavity during systole; and in response to measurement of said parameters of ventricle wall shortening and cardiac output and selectively either in real time or by beat-by-beat computation, determining a desired blood volume and inflow time profile; and controlling a rate and profile of blood inflow of the respective blood displacement actuator during step (b).

9. The method defined in claim 1, further comprising inserting said cannula into a failing ventricular cavity at the apex thereof or at another site of a respective wall affording access without interference with papillary muscle and ventricle valve apparatus or cardiac circulatory or conductive systems.

* * * * *